(12) United States Patent
Terwilliger

(10) Patent No.: US 7,085,653 B2
(45) Date of Patent: *Aug. 1, 2006

(54) METHOD FOR REMOVING ATOMIC-MODEL BIAS IN MACROMOLECULAR CRYSTALLOGRAPHY

(75) Inventor: Thomas C. Terwilliger, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 326 days.

This patent is subject to a terminal disclaimer.

(21) Appl. No.: 10/017,643

(22) Filed: Dec. 12, 2001

(65) Prior Publication Data

US 2002/0116133 A1    Aug. 22, 2002

Related U.S. Application Data

(63) Continuation-in-part of application No. 09/769,612, filed on Jan. 23, 2001, now Pat. No. 6,721,664, which is a continuation-in-part of application No. 09/512,962, filed on Feb. 25, 2000, now Pat. No. 6,931,329.

(60) Provisional application No. 60/275,753, filed on Mar. 14, 2001.

(51) Int. Cl.
G06F 19/00 (2006.01)
G01N 33/48 (2006.01)
G01N 31/00 (2006.01)
G06G 7/48 (2006.01)

(52) U.S. Cl. .............................. 702/27; 702/19; 702/22; 703/11

(58) Field of Classification Search .................. 702/27, 702/19, 20; 703/11
See application file for complete search history.

(56) References Cited

U.S. PATENT DOCUMENTS 5,353,236 A * 10/1994 Subbiah ...................... 364/499
6,721,664 B1 * 4/2004 Terwilliger ................... 702/19

OTHER PUBLICATIONS

Murshudov et al. "Refinement of Macromolecular Structure by the Maximum-Likelihood Method" Acta Cryst. (1997) D53, pp. 240-255.*
Roberts et al., "Phase Improvement by Cross-validated Density Modification", Acta Cryst. (1995), D51, Abstract only.*
Roversi et al., "Modeling Prior Distribution of Atoms for Macro-molecular Refinement and Completion," Acta Cryst. (2000), D56, pp. 1316-1323.
Wang et al., "Crystal Structure Determination of *Escherichia coli* ClpP Starting from an EM-Derived Mask," Journal of Structural Biology, 124, pp. 151-163 (1998).
Beran et al., "Simulated Annealing for Phasing Using Spatial Constraints," Acta Cryst. (1995). A51, 20-27.
Van der Plas et al., "Ab Initio Phasing in Protein Crystallography," Proc of SPIE, (2000) 4123, pp. 249-260.
Read, "Improved Fourier Coefficients for Maps Using Phases form Partial Structures with Errors," Acta Cryst. (1986), A42, pp. 140-149.
Cowtan et al., "Improvement of Macromolecular Electron-Density Maps by the Simultaneous Application of Real and Reciprocal Space Constraints," Acta Cryst. (1993), D49, pp. 148-157.
Terwilliger, "Maximum-likelihood Density Modification," Acta Cryst. (2000), D56, pp. 956-972.
Terwilliger, "Reciprocal-space Solvent Flattening," Acta Cryst. (1999), D55, pp. 1863-1871.
Szoke, "Holographic Methods in X-ray Crystallography, II, Detailed Theory and Connection to Other Methods of Crystallography," Acta Cryst., (1993), A49, 853-866.
Maalouf, "Holographic Methods in X-ray Crystallography, III. First Numerical Results," Acta Cryst., (1993), A49, 866-871.
Beran, "Simulated Annealing for Phasing using Spatial Constraints," Acta Cryst., (1995), A51, 20-27.
Szoke et al., "Holographic Methods in X-ray Crystallography, IV. A Fast Algorithm and its Application to Macromolecular Crystallography," Acta Cryst., (1995), A51, 691-708.
Szoke et al., "Holographic Methods in X-ray Crystallography, V. Multiple Isomorphous Replacement, Multiple Anomalous Dispersion and Non-crystallographic Symmetry," Acta Cryst., (1997), A53, 291-313.

(Continued)

Primary Examiner—John S. Brusca
Assistant Examiner—Eric S. DeJong
(74) Attorney, Agent, or Firm—Ray G. Wilson; Mark N. Fitzgerald

(57) ABSTRACT

Structure factor bias in an electron density map for an unknown crystallographic structure is minimized by using information in a first electron density map to elicit expected structure factor information. Observed structure factor amplitudes are combined with a starting set of crystallographic phases to form a first set of structure factors. A first electron density map is then derived and features of the first electron density map are identified to obtain expected distributions of electron density. Crystallographic phase probability distributions are established for possible crystallographic phases of reflection k, and the process is repeated as k is indexed through all of the plurality of reflections. An updated electron density map is derived from the crystallographic phase probability distributions for each one of the reflections. The entire process is then iterated to obtain a final set of crystallographic phases with minimum bias from known electron density maps.

7 Claims, 11 Drawing Sheets

OTHER PUBLICATIONS

Szoke, "Use of Statistical Information in X-ray Crystallography with Application to the Holographic Method," Acta Cryst., (1998), A54, 543-562.

Bi-Cheng Wang, "Resolution of Phase Ambiguity in Macromolecular Crystallography," Methods in Enzymology, vol. 115, pp. 90-113, 1985.

Shibin Xiang et al., "Entropy Maximization Constrained by Solvent Flatness: a New Method for Macromolecular Phase Extension and Map Improvement," International Union of Crystallography, D49, pp. 193-212, 1993.

G. Bricogne, "Maximum Entropy and the Foundations of Direct Methods," International Union of Crystallography, A40, pp. 410-445, 1984.

G. Bricogne, A Bayesian Statistical Theory of the Phase Problem. 1. A Multichannel Maximum-Entropy Formalism for Constructing Generalized Joint Probability Distribution of Structure Factors, A44, pp. 517-545, (1988).

Thomas C. Terwilliger et al., "Automated MAD and MIR Structure Solution", International Union of Crystallography, D55, pp. 849-861, (1999).

V. Yu. Lunin "Electron-Density Histograms and the Phase Problem," International Union of Crystallography, D49, pp. 90-99, (1993).

Drenth, "Principles of Protein X-Ray Crystallography," Springer-Velag New York, (1994), pp. 1-19.

* cited by examiner

US 7,085,653 B2

METHOD FOR REMOVING ATOMIC-MODEL BIAS IN MACROMOLECULAR CRYSTALLOGRAPHY

RELATED APPLICATIONS

This application claims the benefit of U.S. provisional patent application Ser. No. 60/275,753 filed Mar. 14, 2001; and is a continuation-in-part of U.S. patent application Ser. No. 09/769,612, filed Jan. 23, 2001, now U.S. Pat. No. 6,721,664, issued Apr. 13, 2004, which in turn is a continuation-in-part of U.S. patent application Ser. No. 09/512,962, filed Feb. 25, 2000, now U.S. Pat. No. 6,931,329 all incorporated by reference and made a part of the disclosure herein.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to the determination of crystal structure from the analysis of x-ray diffraction patterns, and, more particularly, to identification of protein crystal structure represented by electron density maps.

BACKGROUND OF THE INVENTION

The determination of macromolecular crystal structures, e.g., proteins, by x-ray diffraction crystallography is a powerful tool for understanding the arrangement and function of such macromolecules. Very powerful experimental methods exist for determining crystallographic features, e.g., structure factor amplitudes and phases. While the structure factor amplitudes can be determined quite well, it is frequently necessary to improve or extend the phases before a realistic atomic model of the macromolecule, such as an electron density map, can be built.

Many methods have been developed for improving the x-ray diffraction pattern phases by modifying initial experimental electron density maps using prior knowledge of characteristics expected in these maps. The fundamental basis of density modification methods is that there are many possible sets of structure factors (amplitudes and phases) that are all reasonably probable based on the limited experimental data that is obtained from a particular experiment, and those crystal structure factors that lead to maps that are most consistent with both the experimental data and the prior knowledge are the most likely overall. Atomic models are commonly used to calculate phases in macromolecular crystallography. Combined with measured amplitudes, model-based phases yield electron density maps with features of the correct crystal structure, but with a significant bias towards features embodied in the model.

Density modification techniques are a firmly established and important tool for macromolecular protein structure determination. These methods include such powerful approaches as solvent flattening, non-crystallographic symmetry averaging, histogram matching, phase extension, molecular replacement, entropy maximization, and iterative model building. The central basis of prior art approaches is that prior knowledge about expected values of the protein electron density in part or all of the unit cell can be a very strong constraint on the crystallographic structure factors. For example, prior knowledge about electron density often consists of the identification of a region where the electron density is flat, due to the presence of disordered solvent. Real-space information of this kind has generally been used to improve the quality of crystallographic phases obtained by other means, such as multiple isomorphous replacement or multiwavelength experiments, but phase information from such real-space constraints can sometimes be so powerful as to be useful in ab initio phase determination.

U.S. patent applications Ser. No. 09/512,962 and Ser. No. 09/769,612, related cases herein, teach maximum-likelihood density modification, a method for carrying out electron density modification in which the phasing information coming from various sources is explicitly kept separate from experimental structure factor amplitudes. This separation of phasing information allowed a statistical formulation for electron density modification that was very straightforward and avoided major existing difficulties with density modification. In maximum-likelihood density modification, the total likelihood of a set of structure factors $\{F_h\}$ is defined in terms of three quantities: (1) any prior knowledge from other sources about these structure factors, (2) the likelihood of measuring the observed set of structure factors $\{F_h^{OBS}\}$ if this set of structure factors were correct, and (3) the likelihood that the map resulting from this set of structure factors $\{F_h\}$ is consistent with prior knowledge about this and other macromolecular crystal structures. This can be written as, $$LL(\{F_h\}) = LL^O(\{F_h\}) + LL^{OBS}(\{F_h\}) + LL^{MAP}(\{F_h\}) \qquad \text{Eq. 1}$$

where $LL(\{F_h\})$ is the log-likelihood of a possible set of crystallographic structure factors $F_h$; $LL^O(\{F_h\})$ is the log-likelihood of these structure factors based on any information that is known in advance, such as the distribution of intensities of structure factors; $LL^{OBS}(\{F_h\})$ is the log-likelihood of these structure factors given the experimental data alone; and $LL^{MAP}(\{F_h\})$ is the log-likelihood of the electron density map resulting from these structure factors. In this formulation, electron density modification consists of maximizing the total likelihood $LL(\{F_h\})$ given by Equation 1.

The total likelihood in Equation 1 can be maximized efficiently by an iterative procedure in which a probability distribution for each phase is calculated independently of those for all other phases in each cycle of the iteration. In one cycle of optimization, an electron density map is calculated using current estimates of the structure factors. Then each structure factor is considered separately from the others, and a phase probability distribution for that structure factor is calculated from the variation of the total likelihood in Equation 1 with the phase (or phase and amplitude) of that structure factor.

In the '612 application, the map log-likelihood, $LL^{MAP}(\{F_h\})$, and the resulting log-likelihood based electron density is further modified to include information arising from structural motifs identified at particular locations in the unit cell. Then, the log-likelihood of the electron density map can be expressed as $$LL(\rho(x, \{F_h\})) = \ln \begin{bmatrix} p(\rho(x)|PROT)p_{PROT}(x) + \\ p(\rho(x)|SOLV)p_{SOLV}(x) + \\ p(\rho(x)|H)p_H(x) \end{bmatrix} \qquad \text{Eq. 2}$$

where $p_H(x)$ refers to the probability that there is a structural motif at a known location, with a known orientation, somewhere near the point x, and $p(\rho(x)|H)$ is the probability distribution for electron density at this point given that this motif actually is present.

Model bias is a very serious problem in macromolecular protein crystallography. A bias in phases that leads to electron density patterns that are incorrect, yet look like features of a protein macromolecule, is very difficult to detect. Such a bias is much more serious than an equivalent amount of noise in a map that is distributed in a random fashion in the unit cell. Bias of this kind commonly occurs when crystallographic phases are calculated based on a model that contains atoms that are incorrectly placed. Maps that are based on these phases tend to show peaks at the positions of these atoms even if the correct electron density would not.

Many methods for reducing model bias in electron density maps have been developed. One of the most widely-used approaches is the $\sigma_A$ method of Read, *Acta Cryst.* A42, pp. 140–149 (1986), in which the weighting and amplitudes of structure factors (but not the phases) are optimized for minimizing effects of model bias. As the phases remain based on the model, $\sigma_A$ weighting retains some model bias. Another important method is the use of omit maps, in which all atoms in a region of the unit cell in the model are removed before using the model to calculate phases. This method reduces model bias, but leads to electron density maps that are intrinsically much noisier than those calculated with all atoms present. Omit maps can still contain some model bias despite the omission of atoms in a region of space, as refinement can adjust the parameters describing all the other, atoms in such a way as to leave a "memory" of the coordinates of the omitted atoms. This memory in omit maps corresponds to the model bias described above that can occur in the first few cycles of map-likelihood phasing. The residual bias in omit maps can be reduced by simulated annealing if the resolution of the data and the accuracy of the starting model allows atomic refinement. Maximum-likelihood refinement of the model structure can also be used to reduce model bias even in cases where $\sigma_A$-weighted electron density maps are not interpretable.

Various objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

Structure factor bias in an electron density map for an unknown crystallographic structure is minimized by using information in generated electron density maps to elicit expected structure factor information rather than relying heavily on structure factor information in a known, similar crystallographic structure. Observed structure factor amplitudes are obtained from x-ray diffractions for a plurality of reflections from the crystal structure. A starting set of crystallographic phases is selected from a model or other source to combine with the observed structure factor amplitudes to form a first set of structure factors. A first electron density map is derived from the first set of structure factors and features of the first electron density map are identified to obtain expected distributions of electron density. The first electron density map is compared with the expected distribution of electron density and an estimate is made how changes in the crystallographic phase of a reflection k affect the comparison. Crystallographic phase probability distributions are established from the comparisons for the possible crystallographic phases of reflection k, and the process is repeated as k is indexed through all of the plurality of reflections. An updated electron density map is derived using crystallographic phases determined to be most probable from the crystallographic phase probability distributions for each one of the reflections. The entire process is then iterated to obtain a final set of crystallographic phases with minimum bias from known electron density maps.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION

Figure 1:
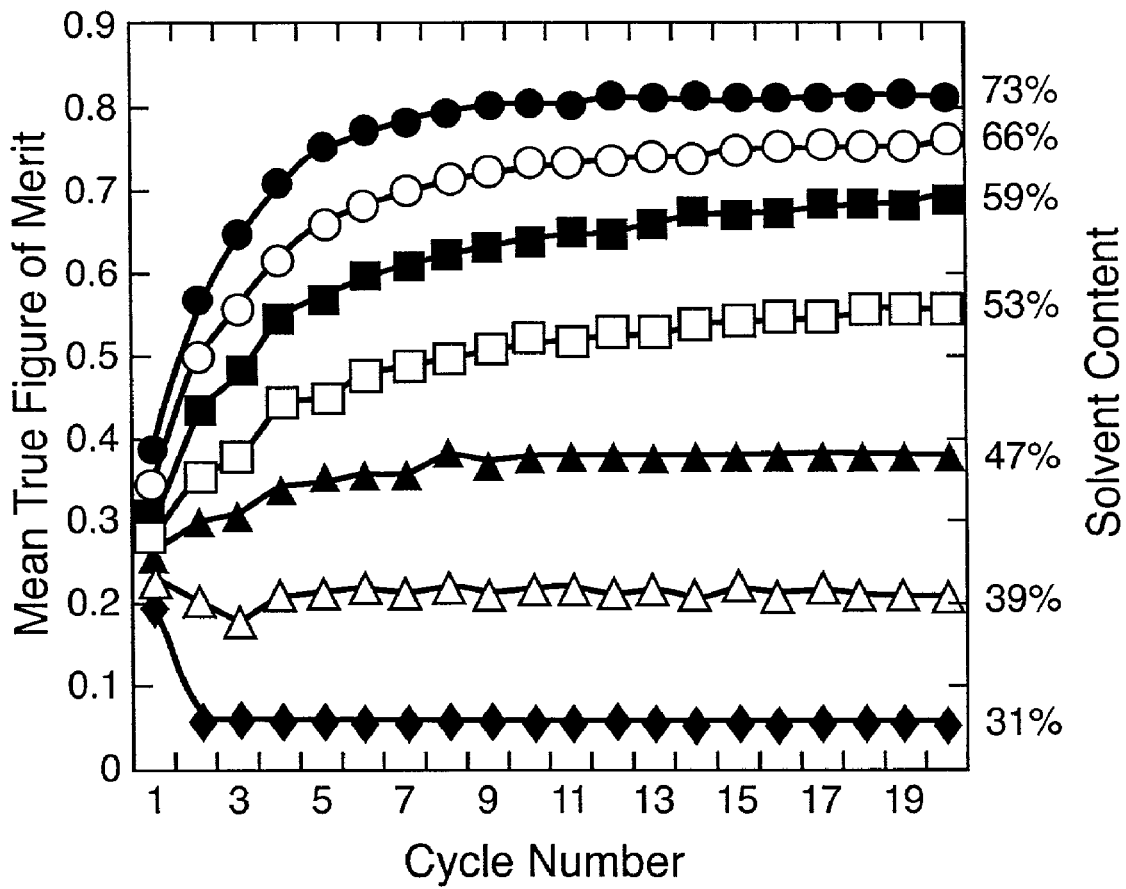
FIG. 1 graphically illustrates the effect of solvent content on accuracy of map-likelihood phasing.

In previous applications of the maximum-likelihood density modification approach, phase information was derived from a combination of experimental probabilities and from known characteristics of the map. In principle, however, experimentally derived or other prior phase information does not necessarily need be included in the maximum-likelihood density modification procedure. Instead, phase information can be derived from the agreement of the map with general expectations alone.

The overall procedure for one cycle of map-likelihood phasing according to the present invention has five basic steps that are based on the methods taught by the "612 application for maximum-likelihood density modification. First, a starting set of phases is used in combination with observed x-ray diffraction structure factor amplitudes to calculate a figure-of-merit weighted electron density map. This map is important because a comparison of this map with expected electron density distributions in the unit cell will form the basis for the determination of phase probabilities. Next, the expectations about the electron density distributions in this map are evaluated. As described in more detail below, this can consist of probability distributions for electron density in the protein and solvent regions along with probability estimates of whether each point in the map is within the protein or solvent region, for example. These probability distributions are needed for defining the prior expectations about the electron density map, and therefore the log-likelihood of the map. Third, the overall log-likelihood of this map, and the first and second derivatives of this log-likelihood with respect to electron density at each point in the map, are calculated. These derivatives will be used to predict how the log-likelihood of the map will change as the electron density in the map is changed. Fourth, using the chain rule and a Fast Fourier Transform (FFT)-based algorithm, the first and second derivatives of the log-likelihood of the map with respect to structure factors are calculated. Fifth, for each reflection k, the variation of the log-likelihood of the map with the phase (or phase and amplitude) of the reflection is estimated from these derivatives. This is important in map-likelihood phasing. Through the use of the derivatives of the log-likelihood of the map with respect to the structure factor k, map-likelihood phasing allows relative probabilities to be assigned for each possible value of the phase of reflection k.

In this calculation of the phase probability distribution for reflection k, ordinarily the measured amplitude is kept fixed and the allowed phases for this reflection are sampled at regular intervals (typically increments of 5 to 20 degrees for acentric reflections). In this procedure, the log-likelihood of the map is approximated in terms of a Taylor's series based on the derivatives with respect to structure factors as described in the '962 and '612 applications, preferably with the addition of a cross-term in the Taylor's series as suggested by Cowtan et al., Acta Cryst. D49, pp. 148–157 (1993), incorporated herein by reference.

To the extent that this approximation is accurate (that is, that higher-order terms do not contribute substantially), this phase probability calculation estimates how the log-likelihood of the map will vary with the phase of reflection k without regard to the value of the phase that was used to calculate the original electron density map. Once all five steps in map-likelihood phasing are carried out, it is possible to calculate a new figure-of-merit weighted electron density map using the newly-estimated phase probability distributions. These phases can then be used to initiate a new cycle of map-likelihood phasing. As the phases are modified in this fashion, it is useful to update the analysis of the probability estimates for whether each point in the map is in the protein or solvent region, and any other analyses based on the map. The iteration of phasing and analysis of the map is then continued until phase changes are minimal.

The effect of each cycle in this procedure is to obtain a probability distribution for each phase independently of all the others, based on the agreement of the electron density map with expectations. In the phase probability calculations, all possible values of the phases are considered without any preference for the values used in the previous cycle.

Map-likelihood phasing is related to the methods of Beran et al., Acta Crysta. A51, pp. 20–27 (1995), of van der Plas et al., Proceedings of the SPIE 4123, pp. 249–260 (2000), and of Wang et al., J. Structural Biol. 124, pp. 151–163 (1998) in which crystallographic phases are obtained by matching the electron density in a part of the unit cell to a target value. The method of Beran, supra., which employs simulated annealing to find a set of phases consistent with constraints on electron density, was shown to be capable of ab initio phase determination using a solvent mask. The approaches of Wang, supra., and of van der Plas, supra., which improves upon existing iterative density modification algorithms, were demonstrated to be sufficient to find crystallographic phases consistent with non-crystallographic symmetry and solvent masks. The maximum-likelihood approach described here and in the '612 application differs from these methods in that probabilistic descriptions of the expected electron density are used, allowing a calculation of phase probability distributions rather than searching for a set of phases that is consistent with constraints.

The phase information from the map-likelihood function $LL^{MAP}(\{F_h\})$ comes from the agreement of the electron density map with prior expectations about that map. This agreement depends on the phase of each reflection, in the context of the phases of all other reflections. In the implementation used in maximum-likelihood density modification, the probability (based on the map-likelihood) for a particular structure factor that the phase has a value $\phi$ is given by the relative likelihood of the map obtained with this value of the phase. For example, a simple map likelihood function might be based on defined regions of an electron density map containing the macromolecule (with substantial variations from point to point) and containing solvent (with a very uniform electron density). A value of the phase for a particular reflection k that leads to a map with a relatively flat solvent is more likely to be correct than a phase that does not.

In a more general case, a map-likelihood function can be defined that describes solvent and crystal structure (i.e., "protein") regions of the electron density map and probability distributions for electron density in each such region. Then the probability of a particular phase for a particular reflection is estimated from how well the resulting map matches these expected characteristics. The concept can also be extended further to include non-crystallographic symmetry or any other expected features of the map. A map-likelihood function can be constructed which reflects the extent to which symmetry-related density in the map is indeed similar, for example.

A formulation of the map log-likelihood function $LL^{MAP}(\{F_h\})$ that follows this approach ('962 and '612 applications) can be written as the integral over the map of a local log-likelihood of electron density, $LL(\rho(x, \{F_h\}))$, $$LL^{MAP}(\{F_h\}) \approx \frac{N_{REF}}{V} \int_V LL(\rho(x, \{F_h\})) d^3x \qquad \text{Eq. 3}$$

where this local log-likelihood of electron density describes the plausibility of the map at each point. As used in Equation 3, $N_{REF}$ is the number of independent reflections, V is the volume, and $LL(\rho(x\{F_h\}))$ is the log-likelihood of the electron density $\rho$ at each point in the volume.

The local log-likelihood function, in turn, can be expressed in terms of whether the point is in the solvent or protein regions, and the expected electron density distributions in each case. As it is often uncertain whether a particular point x is in a protein or a solvent region, it is useful to write the local map-likelihood function as the sum of the conditional probabilities in which environment the point is located:

$$LL(\rho(x,\{F_h\})) = \ln[p(\rho(x)|PROT)p_{PROT}(x) + p(\rho(x)|SOLV)p_{SOLV}(x)] \qquad \text{Eq. 4}$$

where $p_{PROT}(x)$ is the probability that x is in the protein region, $p(\rho(x)|PROT)$ is the conditional probability for $\rho(x)$ given that x is in the protein region, and $p_{SOLV}(x)$ and $p(\rho(x)|SOLV)$ are the corresponding quantities for the solvent region. The probability that x is in the protein or solvent regions can estimated by a modification of the methods of Wang, *Methods Enzymol.*, 115, pp. 90–112 (1985) and Leslie, *Proceedings of the Study Weekend*, organized by CCP4, pp. 25–32 (1988), as described earlier (Terwilliger, *Acta Cryst*. D55, pp. 1863–1871 (1999)) or by other probability-based methods (Roversi et al., *Acta Cryst*. D56, pp. 1316–1323 (2000)), all incorporated herein by reference.

The probability distributions for electron density given that a point is in the protein or solvent regions are central to map-based phasing. They define the expectations about electron density in the map. These expectations about electron density distributions in the map are not derived from "perfect" maps, but rather from the current electron density map. There are several reasons for doing this. The key reason is that it is unreasonable to expect any value of the phase for a particular reflection to lead to a map matching expectations of a perfect map because the map has large errors from all the other reflections. In particular, the correct value of the phase for reflection k can only be expected to slightly reduce the variation in the solvent region, not to make it perfectly flat. The amount by which the electron density in a solvent region can be expected to be flattened by adjusting just one reflection is dependent on the overall noise in the map. In effect, the expectations about the electron density map include not just the features of a perfect map, but also effects of the errors in all of the structure factors other than the one under consideration. Consequently, for a starting phase set with large phase errors, the target probability distribution of electron density in the solvent region is very broad, while, for a starting phase set that is very accurate, this distribution can be very narrow.

Because the targeted features of the electron density map are only weakly defined for poor starting phase sets, but are more precisely defined for accurate ones, the phase information coming from the map-likelihood function becomes stronger as the phases improve. In essence, the more accurate the starting phases, the less noise in the map, the more precisely the phase of a particular reflection can be expected to lead to a map that matches the characteristics of a perfect map, and the more precisely the values of each phase can be determined.

Somewhat paradoxically, although the quality of the starting phase set is an important factor in determining the phase information that comes from the map, the phase probability for a reflection obtained from map-likelihood phasing is completely unbiased with respect to the prior probabilities for that phase. On the other hand, the map-likelihood phase probability for a reflection can be slightly biased by a model used to calculate all starting phases.

To see how the map-likelihood phase for a reflection can be unbiased with respect to prior probabilities for that phase, consider using map-likelihood phasing to obtain a probability distribution for the phase of reflection k. In order to make the situation clear, the procedure described will be a little simpler than the one used in practice. First, calculate an electron density map using all reflections other than k. This map clearly has no bias towards the prior value for reflection k, as reflection k was not even used to obtain the map. Now examine all possible phases of the reflection k in question. For each phase, add to the map the electron density that would result from reflection k with this phase. Then compare the characteristics of the resulting electron density map with the ones that are expected, given the location of solvent and macromolecule and given the expected distributions of electron density in solvent and protein regions. Some values of the phase of reflection k will generally lead to more plausible maps than others. This defines the probability distribution for the phase of reflection k, and the process has made no use whatsoever of any prior information about this reflection. Consequently the resulting phases are completely unbiased with respect to any prior information about reflection k. In practice, this cross-validation procedure is carried out with all the reflections at once employing an approximation and an FFT-based method described in the '962 and '612 applications. The resulting phase probability distributions are essentially the same as the ones described above, however.

Although each individual phase probability distribution obtained with map-likelihood phasing is independent of the prior phase probability distribution for that reflection, there are kinds of bias that can affect map-likelihood phasing. If the set of phases used to initiate map-likelihood phasing has been adjusted as a whole in a way that leads to a relatively flat solvent region, for example, then the first few cycles of map-likelihood phasing will tend to find these starting phases to be probable ones (because they lead to a flat solvent when combined with all the other starting phases) even if these starting phases are incorrect. This situation can occur for example if a model has been used to calculate the starting phases, as the solvent region will tend to be relatively flat even if the model is not entirely correct. It can also occur if the phases have been refined in order to flatten the solvent region. Fortunately, as described below, this type of model bias is generally removed by iterative application of map-likelihood phasing.

As described above, other approaches to using expectations about electron density distributions in a map for determining crystallographic phases without including phase probability distributions from other sources have been demonstrated. Each of these approaches begins with no prior phase information and is designed to result in an ab initio phase determination. These approaches could be modified to begin with a starting phase set as described here for map-likelihood phasing; however, the probability-based approach described here is more general and can include a variety of expectations about the map. Additionally, map-likelihood phasing leads to phase probability distributions rather than phases consistent with expectations, so that optimally-weighted maps can be calculated.

Map-likelihood phasing has the potential for producing electron density maps that have little or no bias, as the phase probabilities for each reflection are independent of the prior phases for that reflection. However, it is possible for map-likelihood phasing to be biased by a starting phase set that has a systematic bias, for example by a starting set of incorrect phases that has a relatively flat solvent region. The iteration of cycles of map-likelihood phasing is a useful tool in reducing or eliminating this bias. The reason for expecting that an iterative application of map-likelihood phasing would remove the bias present in a single cycle is that the bias for an individual reflection comes from the set of starting phases as a whole. Once many of the phases in the set are substantially changed, the bias is expected to be greatly reduced.

There are two general cases that could arise in carrying out iterative cycles of map-likelihood phasing. If the solvent content or non-crystallographic symmetry are high, then the phases are likely to be well-determined, and simple iterative map-likelihood phasing would be effective. If the solvent content is low and non-crystallographic symmetry is lacking, however, the phases might not be entirely determined by the map-likelihood function. In this case it might be necessary to trade off a small bias towards the starting phase set in order to obtain a well-defined set of phases.

Introducing a small bias towards the prior phase probabilities can be understood in the context of maximum-likelihood density modification. In maximum-likelihood density modification, the prior phase probabilities are used together with the map-likelihood phase probabilities described here, with equal weighting of the two terms. If the prior and map-likelihood phase probabilities are appropriately calculated, then these phases will have more correct phase information than either the prior or map-likelihood phases alone. These are the best possible phases using the available information. On the other hand, these phases are partly based on the starting phase information, which in some cases may have serious model bias.

In contrast, in pure map-likelihood phasing, the weight on the prior phases is zero. These phases may not be the most informative possible, but (as shown below) they are essentially unbiased with respect to the starting phases or model. Finally, in map-likelihood phasing with a slight bias towards prior phases, the weight on the prior phases might have some small, but non-zero value. The higher the value of this weighting factor, the more accurate the phases, but the larger the bias towards the model. In effect, the weighting on the prior phases (see below) would determine the amount of bias that is accepted in order to obtain well-determined phases.

As shown in the next section, map-likelihood phasing can effectively reduce model bias in map-likelihood phasing in cases where the solvent content is about 40% or greater. In cases with lower solvent content, iterative map-likelihood phasing does not always converge to a unique set of phases, and a small bias towards the starting phase probabilities is helpful.

In order to evaluate the range of applicability of map-likelihood phasing and the utility of iterative phase improvement with this technique, several tests were carried out with model data, where the quality of phasing could readily be assessed. FIGS. 1 and 2A–C illustrate the convergence properties of map-likelihood phasing as a function of percentage of the asymmetric unit that is occupied by disordered solvent. Model datasets were constructed based on the refined structure of dehalogenase enzyme from {Rhodococcus} as described in Terwilliger, Acta Cryst. D56, pp. 965–972 (2000). To simulate varying amounts of solvent, varying numbers of water molecules and C-terminal residues were left out of the phase calculations. This led to models with solvent content ranging from 31% (as in the actual crystals) to 73%. Starting phase sets with simulated errors were constructed and used along with the model amplitudes in map-likelihood phasing. In these simulations, a mask defining the solvent and protein regions was calculated from the atomic coordinates in the model, defining all points within 2.5 Å of an atom as being within the protein region. In each test, 20 cycles of phase calculation followed by figure-of-merit weighted map calculation were carried out. For each cycle, the mean twe figure of merit, given by the cosine of the phase error ($\cos \Delta\phi$) is plotted.

FIG. 1A shows the effect of the percentage of the cell occupied by the macromolecule and by "solvent" (actually simply absence of protein in these simulations) on the phases obtained from map-likelihood phasing. The starting mean true figure of merit in each case was 0.32. For simulations with about 50% solvent or greater, each cycle of map-likelihood phasing resulted in phases that were at least as accurate as those in the previous cycle, with convergence essentially complete within 20 cycles. For those with 39% solvent, the phases became slightly worse with map-likelihood phasing compared to the starting phases, and for the case with 31% solvent, they were considerably worse.

Figure 2A:
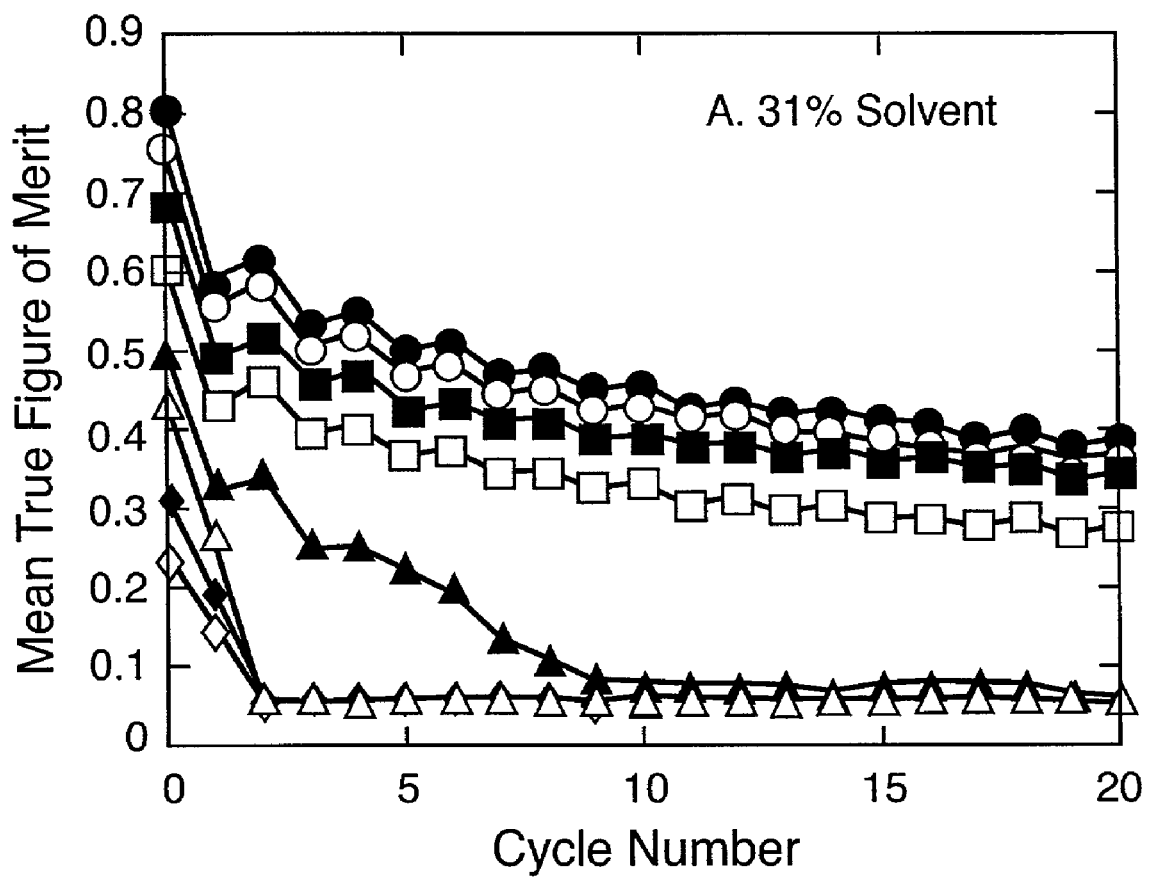
FIGS. 2A–C graphically illustrate the effect of starting phase accuracy on the accuracy of map-likelihood phasing with 31%, 47%, and 71% solvent content, respectively.
Figure 2B:
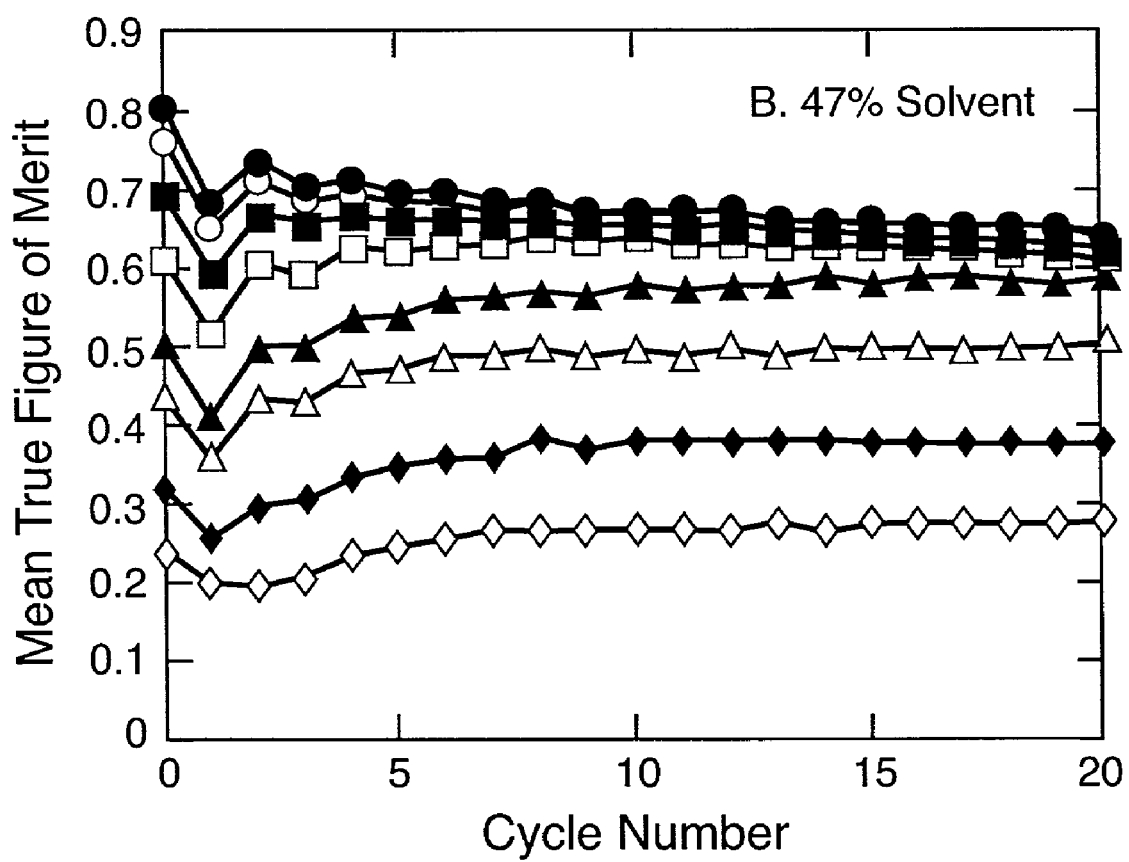

FIGS. 2A and 2B expand on the simulation shown in FIG. 1, illustrating the stability and convergence of phasing beginning with phases with varying errors, for solvent content of 31%, 47%, and 73%. In the case of 31% solvent content, for all starting phase sets the quality of phases generally decreased with each cycle of map-likelihood phasing. In contrast, for the simulation with 47% solvent the quality of phases increased slightly with each cycle. Starting from phase sets with a true figure of merit of about 0.4 or greater, all of the test simulations converged to phase sets with similar true figures of merit of about 0.6. For 73% solvent, the quality of the phases reached the same very high true figure of merit of about 0.8, regardless of the true figure of merit of the starting set of phases in the range of 0.3 to 0.8.

Figure 3:
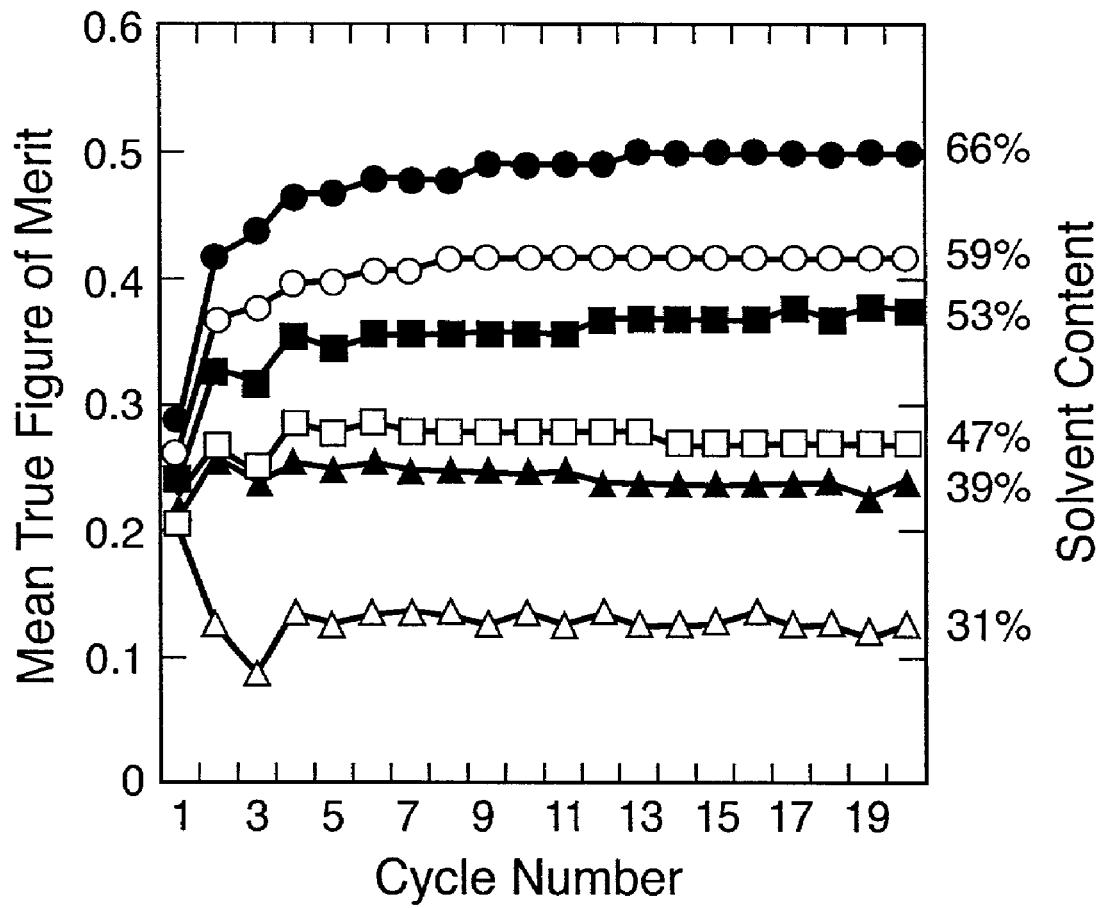
FIG. 3 graphically illustrates the effect of solvent content on map-likelihood phasing with a partially incorrect mask.

FIG. 3 illustrates the effect of errors in the definition of solvent and protein regions on phasing. The simulations in this figure were carried out in the same way as those in FIG. 1, except that the mask used was based on a model that was missing about 10% of the atoms, so that about 10% of the "protein" region was classified as "solvent". The quality of the map-likelihood phases obtained was less than that obtained with the correct mask, but still, in the cases with about 50% or greater solvent content, the phase quality improves with map-likelihood phasing over the starting phase set.

Figure 2C:
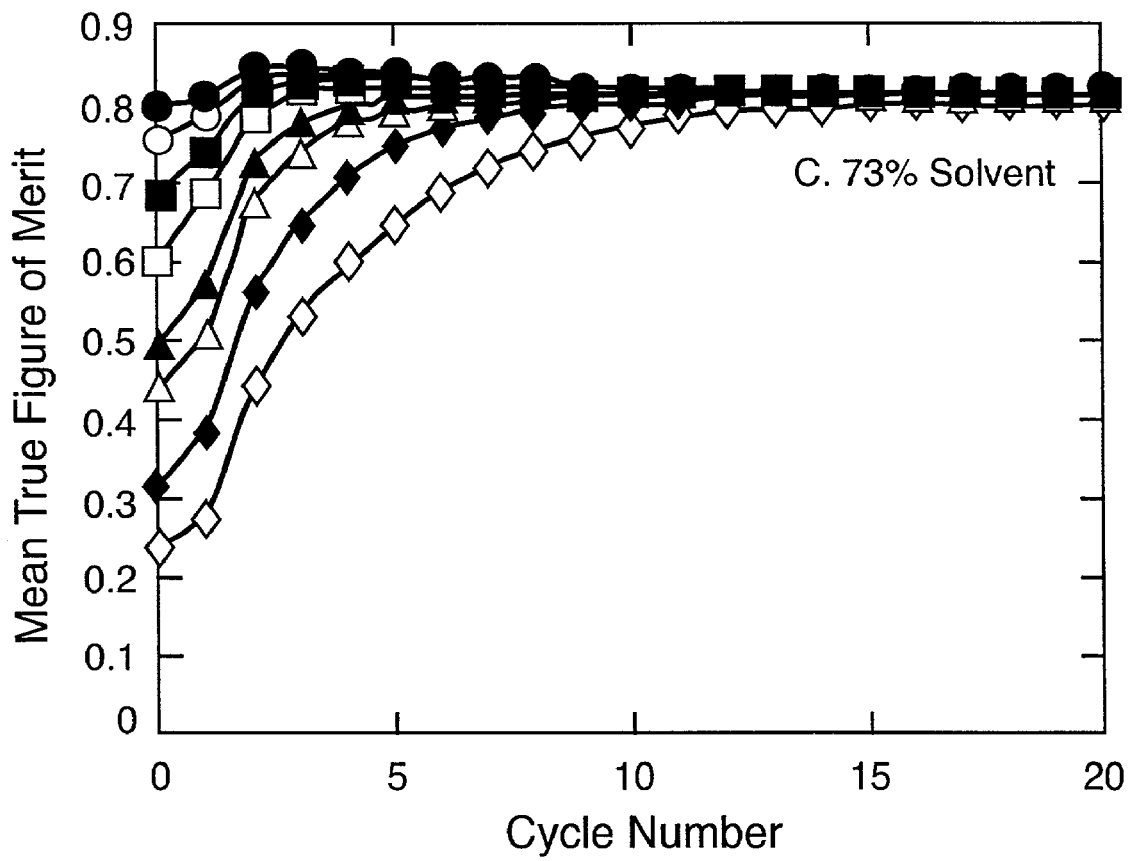
Figure 4:
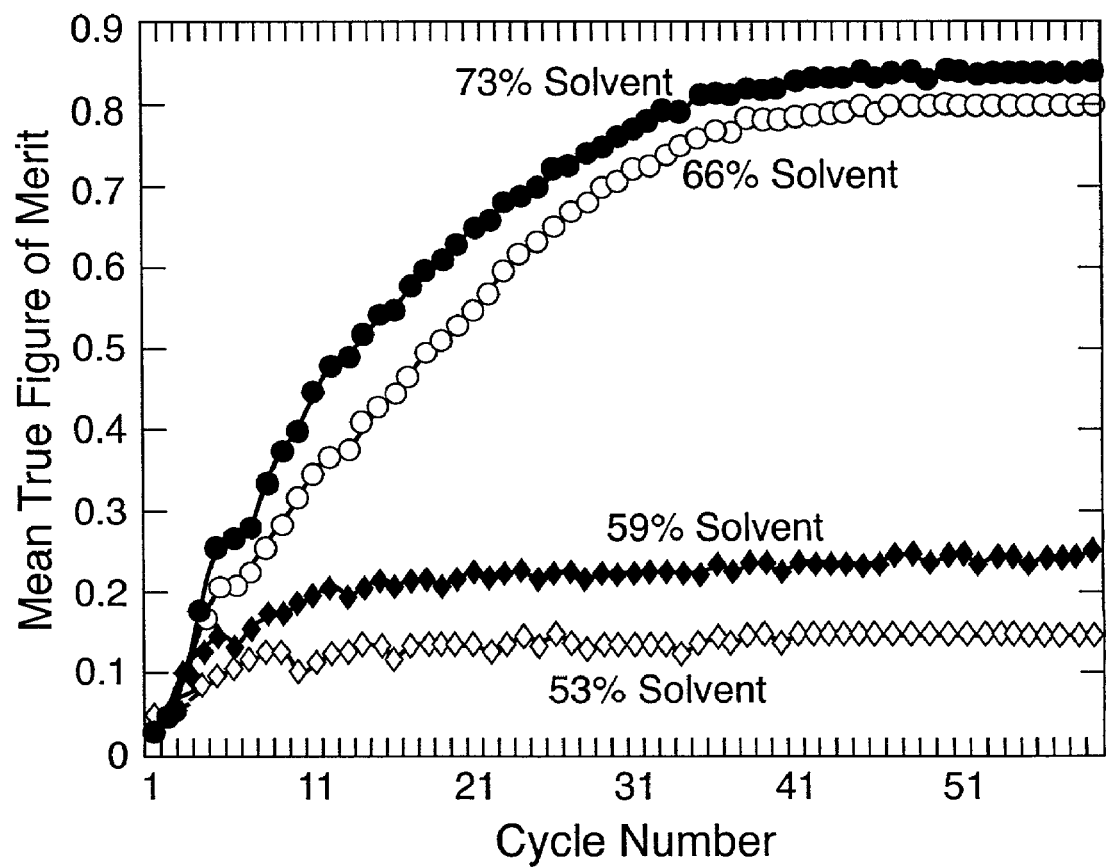
FIG. 4 graphically illustrates the effect of solvent content on map-likelihood phasing with no prior phase information.

FIG. 2C shows that in cases with very high solvent content (73%), map-likelihood phasing yielded very substantial phase improvements, and converged to essentially the same point regardless of the starting phase set used. FIG. 4 shows this further by illustrating the phase quality obtained by map-likelihood phasing as a function of solvent content, beginning with zero phase information (a blank map), but with a perfect solvent mask calculated from the atomic model. FIG. 4 shows that in cases with 66% and 73% solvent, map-likelihood phasing is sufficient in itself to determine crystallographic phases with high accuracy. In the model cases with 59% and 53% solvent, a modest improvement in phase quality was obtained. It should be noted that, although the map-likelihood approach was successful in ab initio phasing when using model data, tests carried out so far with experimental data have not resulted in substantial phase improvement. Presumably this is due to complications from measurement errors and from the smaller differentiation between solvent and protein regions in real crystals compared to the model datasets examined here.

A very important feature of map-likelihood phasing is the potential for reducing or eliminating model bias in electron density map calculations. Test cases with model data were set up in order to examine how thoroughly model bias could be removed using iterative map-likelihood phasing, and how this depended on the solvent content of the crystal. At the same time, the effect of including a small amount of prior phase information on bias and map quality for various solvent contents was examined.

Model datasets were constructed using the refined structure of dehalogenase enzyme from {Rhodococcus}, and leaving out varying numbers of water molecules and atoms from the C-terminums to simulate varying amounts of solvent content as in FIG. 1. These models were considered the "correct" structures in the tests. Then from each correct model, a "molecular replacement" model was constructed by varying the coordinates of atoms in the correct model by an r.m.s.d. of 1.4 Å, using a function that varied sinusoidally in space so that the connectivity of the molecule remained intact. Next, all the atoms in the molecular replacement model that were placed incorrectly were identified by noting the value of the electron density in a "perfect" map calculated with structure factors based on the correct model. All those atoms in the molecular replacement model that were in density from $-0.5\sigma$ to $0.5\sigma$ were considered to be incorrectly placed. From 20% to 30% of the atoms in the molecular replacement models were incorrectly placed according to this criterion. The mean density at coordinates of these incorrectly placed atoms in the perfect electron density maps for the simulations with various solvent content ranged from $0.03\sigma$ to $0.06\sigma$, and the mean density at the coordinates of atoms in the correct model in the perfect electron density map ranged from $1.7\sigma$ to $2.9\sigma$, with the higher values corresponding to higher solvent contents (in which most of the cell is solvent, so the ratio of peak height to the r.m.s. of the map is higher even with perfect data).

Figure 5A:
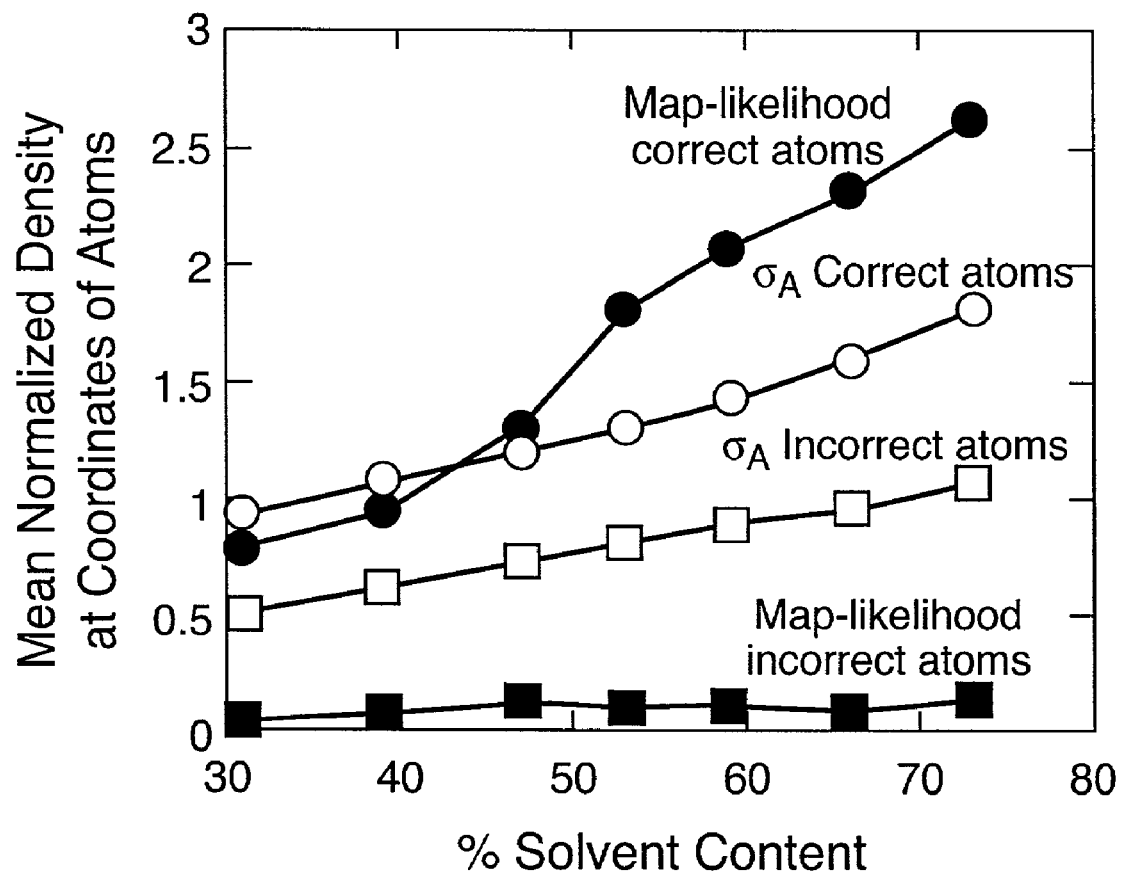
FIGS. 5A and 5B graphically compares map-likelihood phasing with phases calculated with $\sigma_A$-weighting showing electron density at correctly placed atoms and the ratio of electron density at incorrectly-placed atoms to correctly-placed atoms, respectively.

In the tests of model bias, the overall accuracy of electron density maps in these tests was assessed from the normalized mean value of electron density at the coordinates of atoms in the correct model. The model bias was assessed from the normalized mean value of electron density at coordinates of incorrectly placed atoms in the molecular replacement model used in phasing. FIG. 5A shows the overall accuracy and model bias obtained by map-likelihood phasing (with no prior phase information included in probability calculations) as a function of the solvent content in the model crystals. For comparison, the accuracy and model bias for $\sigma_A$-weighted maps based on the same data are shown. The overall accuracy of both the $\sigma_A$-weighted and map-likelihood phased maps was quite high in all cases, with the map-likelihood phased maps showing greater accuracy in all cases except at very low solvent content. The $\sigma_A$-weighted maps had mean values of electron density at coordinates of atoms in the correct model ranging from $0.9\sigma$ (31% solvent) to $1.8\sigma$ (73% solvent), while the map-likelihood phased maps had mean values of electron density at coordinates of atoms in the correct model ranging from $0.8\sigma$ (31% solvent) to $2.6\sigma$ (73% solvent).

Figure 5B:
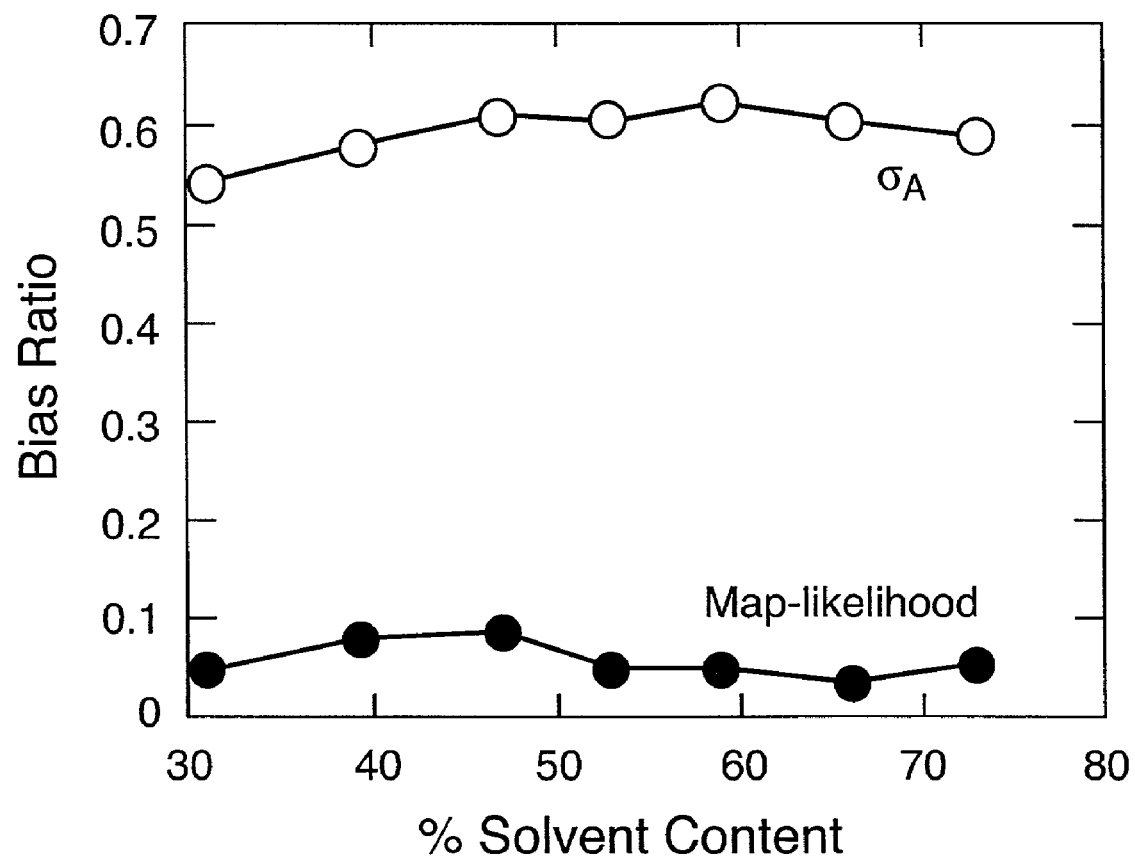

The level of bias was very different in the two methods. The $\sigma_A$-weighted maps had mean values of electron density at coordinates of incorrectly-placed atoms in the molecular replacement model ranging from $0.5\sigma$ (31% solvent) to $1.1\sigma$ (73% solvent). In contrast, the map-likelihood phased maps had values ranging from just $0.04\sigma$ (31% solvent) to $0.13\sigma$ (73% solvent), only slightly higher than the values of $0.04\sigma$ to $0.06\sigma$ found for a perfect map. Overall, the bias ratio, the ratio of the mean values of electron density at incorrectly-placed to correctly-placed atoms for $\sigma_A$-weighted maps was in the range of 0.5 to 0.6 for all values of solvent content (FIG. 5B). The bias ratio using map-likelihood phasing was in the range from 0.03 to 0.09 for all values of the solvent content, indicating that bias was nearly eliminated in all cases.

In the map-likelihood calculations on model data for crystals with high solvent content (73%), the map-likelihood phases converged after just a few cycles, as was shown in FIG. 2C. In contrast, for the test data with very low solvent content (31%), the phases continued to gradually diverge from the starting phase set (FIG. 2A). This lack of convergence for data from crystals with very low solvent content is not surprising, as the information about electron density in the solvent region is insufficient to define the crystallographic phases when the solvent content is low. Although some additional information comes from the expected electron density distributions in the region of the macromolecule, this phase information is considerably weaker than that coming from the solvent. A consequence of the lack of convergence is that the overall quality of the electron density map gradually decreases with iterations of map-likelihood phasing. As discussed above, one way to maintain a high quality of the overall map, yet to keep the level of bias low, is to include the prior phase information from the model in phasing, but using a very low weighting relative to the map-likelihood phases.

Figure 7:
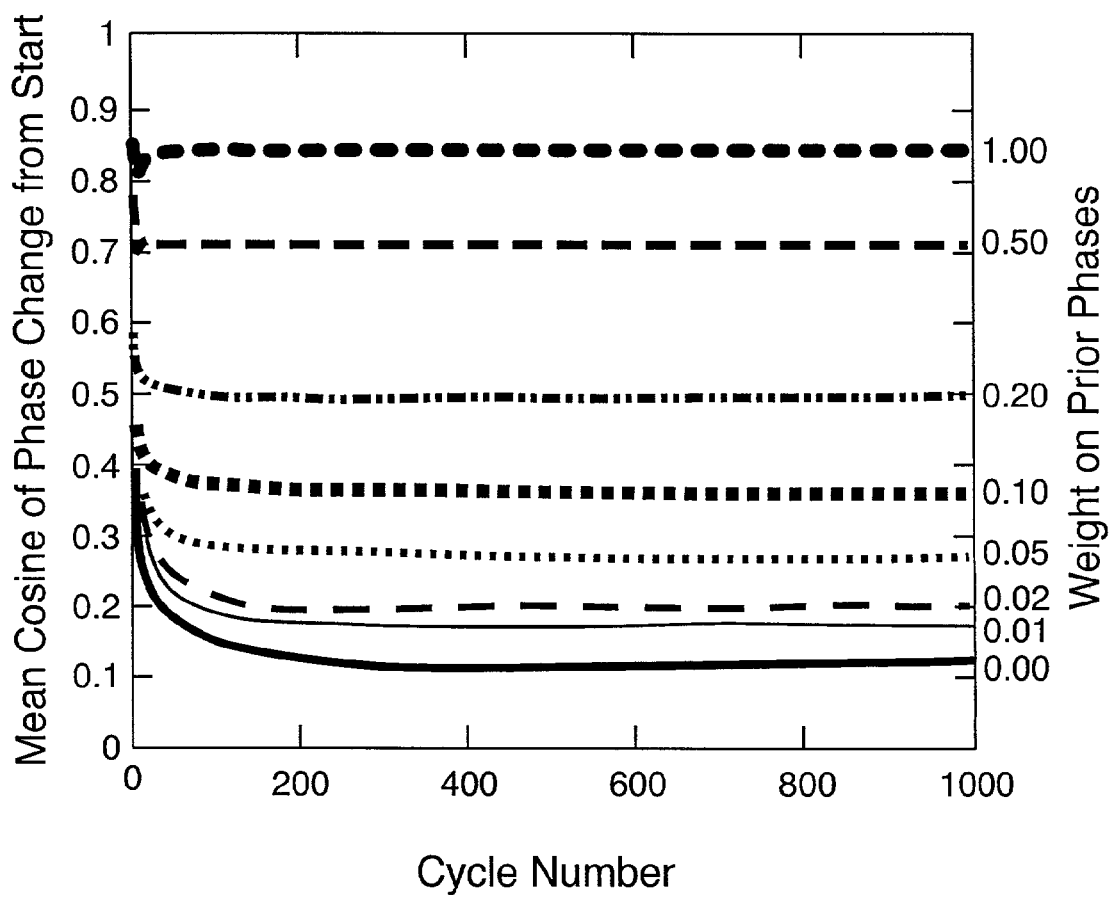
FIG. 7 graphically illustrates the convergence of map-likelihood phasing as a function of solvent content.

FIG. 7 illustrates the overall quality of maps and bias ratios (as in FIG. 5) for map-likelihood phasing with 31%, 47%, and 73% solvent and including varying amounts of prior phase information, ranging from zero weight on prior phases, to equal weighting of prior phases and map-likelihood phases. For the simulations with solvent content of 31% and 47%, the overall quality of the maps generally increases as expected with inclusion of prior phase information, with mean electron density at coordinates of atoms in the perfect model with 31% solvent increasing from 0.89 (zero prior phase information) to 1.09 (1% prior information). When equal weight is placed on the prior information, overall quality decreases slightly, indicating that the prior phase probability distributions may not be quite optimal. For the simulation with 73% solvent, inclusion of prior phase information had only a small, and generally negative, effect on the overall accuracy of phasing. This is presumably due to the very high amount of unbiased phase information in the map-likelihood function in this case of high solvent content.

Figure 6A:
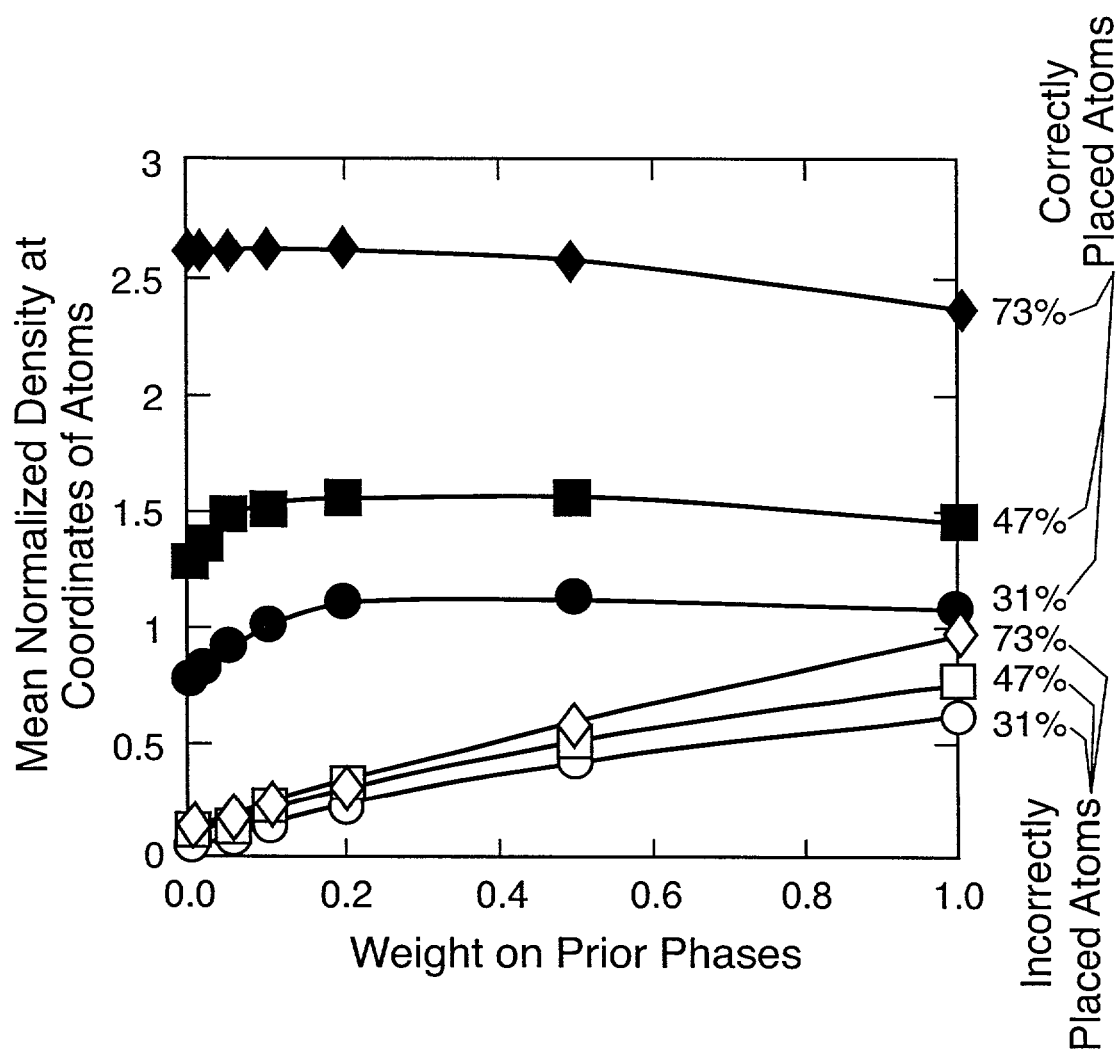
FIGS. 6A and 6B graphically illustrate the effect of including prior phase information on map quality and on map bias, respectively.
Figure 6B:
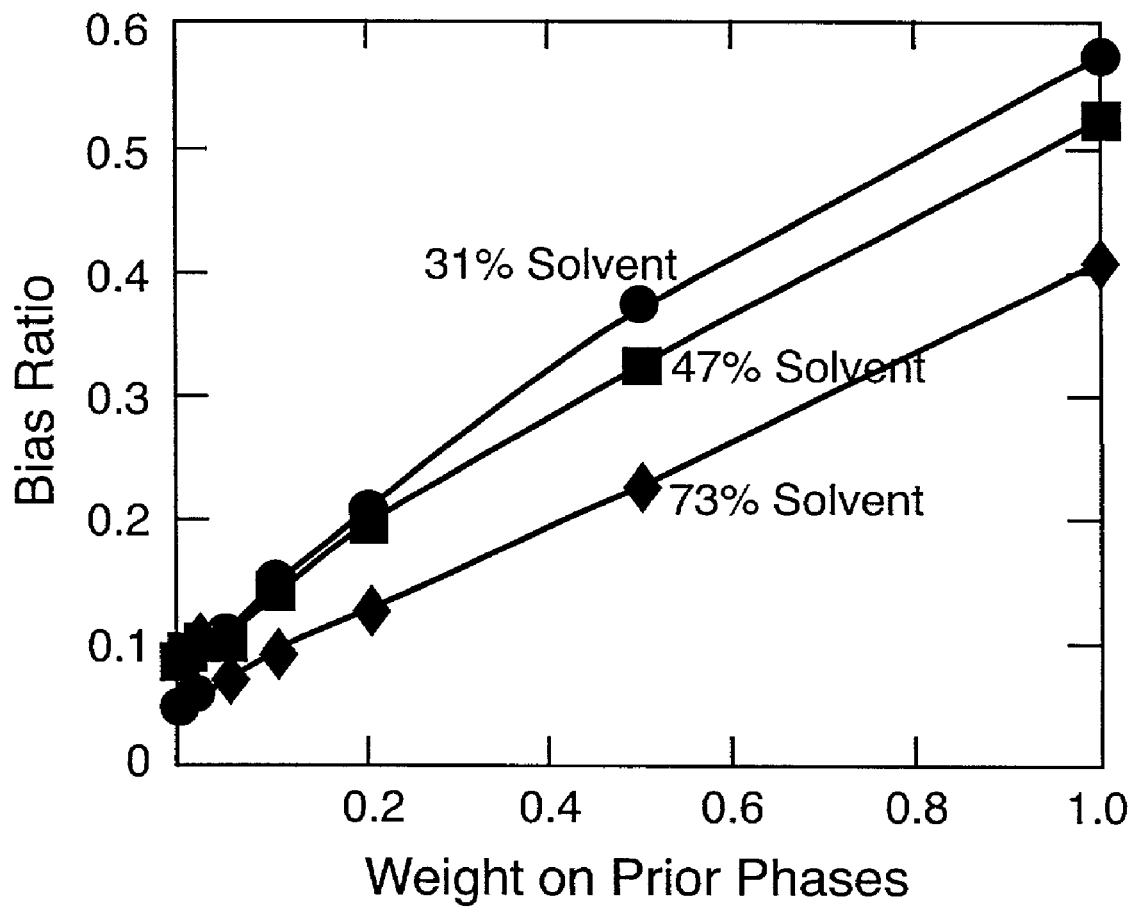

The purpose of including the prior phases with a small weight is to increase the overall accuracy of phasing by including some of the (partially correct) prior phase information, while minimizing the bias that is introduced from this (partially incorrect) prior information. As increasing weight is placed on the prior phases, the ratio of electron density at incorrectly placed atoms to density at correctly-placed atoms (the bias ratio, FIG. 6B) increases. For the simulation with 31% solvent, the bias ratio ranges from 0.47 (zero prior phase information) to 0.068 (1% prior information) to 0.57 (equal weight on prior phase information). A comparison of FIGS. 6A and 6B suggests that for cases with 31% or 47% solvent, the inclusion of prior phase information with a weighting factor of up to about 10% would cause a small increase in bias, from 5% up to 10%–15%, while improving the overall quality of the phasing by about 20%. In some situations, this addition of a small amount of bias would be acceptable in order to achieve the increase in phase quality, while in others it might not.

The addition of a small amount of prior phase information has a substantial effect on the convergence of the map-likelihood phasing procedure, particularly in cases with low solvent content. The convergence of the map-likelihood phasing for solvent content of 31% with some prior phase information is illustrated in FIG. 7. In an ordinary application of map-likelihood phasing, about 40 cycles of iteration would be carried out. In order to examine the convergence properties in more detail, 1000 cycles were carried out for each simulation, with weights on the prior phase information ranging from zero to unity. The procedure does not fully converge without any prior phase information, with substantial changes occurring even after hundreds of cycles of iteration. On the other hand, with as little as a 1% to 10% weight on the prior phases, the procedure converges much more quickly, so that with 10% weight on the prior phases, convergence is essentially complete within the first 40 cycles. Considering the results in FIGS. 6A and 6B, which showed that a small bias towards the prior phases is sufficient to improve the overall quality of the map significantly, it may be concluded that a bias towards the prior phases in this range of 1% to 10% is in many cases likely to be a reasonable balance between minimizing bias and maximizing map quality.

An important application of map-likelihood phasing is likely to be structure validation. An unbiased method of comparing a model with amplitudes of experimental structure factors that can identify specific places in the structure that are not fully compatible with the data would be of great help in structure validation. The map-likelihood phasing method is well-suited to this task as it produces phase probabilities that are essentially unbiased by the starting phase set.

The technique of map-likelihood phasing has potential applications in many situations in X-ray crystallography. The critical characteristics of map-likelihood phasing are (1) that it derives phase information from the agreement of features of the electron density map with expectation, and (2) that it produces phase (or amplitude and phase) probability information that is minimally biased by the starting phase set. The phases it produces are complementary to those obtained by experimental (e.g., MIR, MAD) approaches because the source of phase information is completely separate (e.g., solvent flatness vs MAD measurements). For the same reason, phases are also complementary to phases calculated from a model or partial model by $\sigma_A$-based or related approaches.

The approach is applicable to any situation in which phase probabilities unbiased by a starting phase set are desirable, in which some characteristics of the electron density map can be anticipated in advance. It is most readily applied to cases where a starting set of phases exists, though as shown above, this is not required.

The accuracy of the phases obtained using map-likelihood phasing can be expected to depend largely on two factors. One is the extent of constraints that are known in advance about the electron density map. If the structure contains a very large amount of solvent, for example, then much phase information can be obtained because electron density in the solvent region is very highly constrained. The other is the quality of the starting phase information. In an extreme case, if the phases of all reflections with significant intensities except one were known perfectly, then the phase of the final reflection could be determined perfectly because only the perfect phase would lead to a perfectly flat solvent region. In general, the higher the quality of starting phase information, the better defined the resulting probability distributions.

The degree of bias towards the starting phase set in map-likelihood phasing can be adjusted using a weight on the prior phase probabilities. In cases where the phase information in the map is insufficient to fully define the phases (such as substantially less than 50% solvent content with no non-crystallographic symmetry), it is useful to trade off a small amount of bias in order to increase the accuracy of the phases obtained. This can be accomplished with a weighting of a few percent on the prior phase probability distribution.

It will be understood that the above process is implemented in software to be run on a general purpose computer. In specific situations it might be desirable to implement the process in firmware or other embodiments of a software routine and it is considered such implementations are within the scope of the present invention.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method using density modification to remove atomic model bias of an electron density map representing a crystal structure of a macromolecule comprising:
   (a) obtaining by x-ray diffraction observed structure factor amplitudes for a plurality of reflections from the crystal structure;
   (b) using a starting model of the crystal structure to calculate a starting set of crystallographic phases, and combining the starting set of crystallographic phases with the observed structure factor amplitudes to form a first set of structure factors;
   (c) deriving an electron density map from the current set of structure factors;
   (d) selecting specific features of the electron density map not used in the calculation of the first set of structure factors from the group consisting of: flatness of solvent region, non-crystallographic symmetry, structural motifs, and probability distributions for electron density in solvent regions; and using the specific features to construct probability functions for electron density for each point in the electron density map;
   (e) evaluating the overall probability that the electron density map is correct by making a comparison between the electron density map and the probability functions for electron density for each point in the map;
   (f) estimating how changes in the crystallographic phase of a reflection k affect the comparison;
   (g) establishing crystallographic phase probability distributions from the comparisons for the possible crystallographic phases of reflection k, absent phase information from the starting model of the crystal structure:
   (h) repeating steps (c) through (g) as k is indexed through all of the plurality of reflections;
   (i) determining a set of the most probable crystallographic phases for each one of the reflections from the crystallographic phase probability distributions; and
   (j) deriving an updated electron density map using the observed structure factor amplitudes and the set of crystallographic phases determined to be most probable from the crystallographic phase probability distributions for each one of the reflections;
   (k) repeating steps (d) through (j) with the electron density map replaced with each updated electron density map until changes in the set of crystallograph phases become minimal between successive iterations to obtain a final set of crystallographic phases with minimum bias from known electron density maps; and
   (l) forming a final electron density map using the final set of crystallographic phases.

2. The method of claim 1, wherein identifying features of the electron density map includes making probability estimates of whether each point in the map is located in the solvent region or a region containing the macromolecule.

3. The method of claim 1, wherein identifying features of the electron density map includes estimates of whether the electron density at each point in the map is related by non-crystallographic symmetry to electron density at another point in the map.

4. The method of claim 1, wherein identifying features of the electron density map includes estimates of whether a structural motif is located at each point in the map.

5. The method of claim 4, wherein the structural motif is a helix.

6. The method of claim 1, wherein the step of determining a set of the most probable crystallographic phases further includes the steps of calculating first and second derivatives for the crystallographic phase probability distributions with respect to the structure factors; and applying a Fast Fourier Transform-based algorithm to determine the most probable crystallographic phase probability distributions for the electron density map.

7. The method of claim 1, wherein the step of selecting a starting set of crystallographic phases includes;

selecting a model crystal structure having similarities to the crystal structure being examined;

deriving a set of weighted crystallographic phases by assigning a low weighting factor to the crystallographic phases of the model crystal structure;

using the set of weighted crystallographic phases and combining with the observed structure factor amplitudes to derive the electron density map; and combining the set of weighted crystallographic phases with the crystallographic phase probability distributions from claim 1 step (g) to form a composite set of crystallographic phase probability distributions.

* * * * *